US006360747B1

(12) United States Patent
Velarde et al.

(10) Patent No.: US 6,360,747 B1
(45) Date of Patent: Mar. 26, 2002

(54) PERSONAL PASSIVE RESTRAINT SYSTEM

(76) Inventors: Albert A. Velarde, 832 Los Poblanos La., NW., Albuquerque, NM (US) 87107; Rogelio N. Banez, 900 La Charles NE., Albuquerque, NM (US) 87112

( * ) Notice: Subject to any disclaimer, the term of this patent is extended or adjusted under 35 U.S.C. 154(b) by 0 days.

(21) Appl. No.: 08/923,607

(22) Filed: Sep. 4, 1997

Related U.S. Application Data

(60) Provisional application No. 60/024,692, filed on Sep. 5, 1996.

(51) Int. Cl.$^{7}$ .......... A61B 19/00

(52) U.S. Cl. .......... 128/869; 128/878; 70/16

(58) Field of Search .......... 128/846, 869, 128/876, 878, 879; 70/16

(56) References Cited

U.S. PATENT DOCUMENTS 1,536,551 A * 5/1925 Young
4,422,455 A * 12/1983 Olsen .......... 128/878
4,628,925 A * 12/1986 Witzel .......... 128/878
4,949,679 A 8/1990 Wolfer .......... 119/96
5,345,947 A * 9/1994 Fisher .......... 128/878
5,469,813 A 11/1995 Peden .......... 119/770
5,894,748 A * 4/1999 Capperrune .......... 70/16

* cited by examiner

*Primary Examiner*—Michael A. Brown
(74) *Attorney, Agent, or Firm*—Roger F. Phillips

(57) ABSTRACT

A restraining device for use in securing a prisoner having an upper control strap gripped through a releasable cam buckle and secured to a pair of handcuffs worn by an individual behind his back, the loose end acting as a hand grip. The cam buckle is attached to leg shackles worn on the ankles of the prisoner be means of a lower strap loop of fixed length The length of the upper control strap between the handcuffs and the cam buckle can be adjusted by pulling the control strap through the cam buckle, thus tightening the restraining device relative to the prisoner's wrists and ankles. The overall length can be increased by opening the cam buckle and sliding the buckle along the control strap as desired. A strap lock is located on the loose end of the control strap to be slid to a position against the cam buckle to assure a secure closure thereof. The overall length of the restraining device can be adjusted between a tight position to control a violent prisoner and a loose position to allow the prisoner to stand off balance and walk with assistance and for seating during transport. The adjustability allows for application to prisoners of differing sizes.

7 Claims, 2 Drawing Sheets

PERSONAL PASSIVE RESTRAINT SYSTEM

This is a Continuation-In-Part of provisional application No. 60/024,692 filed Sep. 5, 1996.

BACKGROUND OF THE INVENTION

1. Field of the Invention

The present invention relates to personal restraint devices. More particularly, this invention relates to personal restraint devices useful in law enforcement for the restraint of persons under arrest.

2. Discussion of the Prior Art

Wrist and ankle restraints in the form of lockable cuffs are individually known in the prior art. Such cuffs hold the hands or the feet together or in close proximity to each other, thus, limiting movement of the restrained individual. Such devices, simultaneously used, do not limit the relative movement of hands to feet, resulting in a violent individual's ability to cause damage to property, injury to other persons, and to escape from law enforcement officers, in some instances.

It is also known to provide a strap or belt assembly to restrain an individual by attachment to the wrists and the legs or ankles for location behind an individual. Fisher provides such an assembly (U.S. Pat. No. 5,345, 947) wherein an upper loop mounted on a cam buckle is attached to handcuffs by a snap hook. The cam buckle adjustably engages a strip which forms a loop at one end for engaging an individual's legs or ankles, the other end being free. The Fisher strap system appears to be effective for maintaining an individual in a crouched position where the effective length of the assembly between the wrists and ankles is kept relatively short. The Fisher system would appear to be a relatively ineffective restraint during standing and walking as the loop placed on the legs or ankles of a restrained individual is adjustable and as such would be subject to sliding up the legs of the individual, thus reducing the effectiveness of the Fisher system. The Fisher system appears to be most effective when the restrained individual is relatively immobile. This is a clear drawback when used in a prisoner transportation setting.

Peder provides a restraint system(U.S. Pat. No. 5,469, 813) for placement between wrists and ankles which is not readily adjustable and is apparently intended to restrain and immobilize an individual. The Peder system would be substantially unusable in a prisoner transportation setting.

The assembly of Wolfer(U.S. Pat. No. 4,949, 679) is intended to maintain an individual's wrists at a point near his waist, but fails to provide for connection with the ankles of the restrained individual and thus does not restrain kicking or running, etc.

The present invention severely limits a restrained individual's movements of the hands relative to feet of a restrained individual during periods of violent activity, while providing easy adjustment for application to varying sizes of individuals. The adjustment also allows for convenient easing of restraint for purposes of sitting in an automobile, standing, or walking, or during periods when the restrained individual assumes a peaceful attitude.

SUMMARY OF THE INVENTION

The present invention relates to a personal restraint system useful for the restraint of a person under arrest by law enforcement officers.

An object of the invention is to provide a personal restraint system which limits movement of the restrained individual's hands relative to their feet.

Another object of the invention is to provide a personal restraint system which is easily adjustable to provide for its use on various sized individuals and to allow relaxation of the restraint for purposes of assuming a sitting position.

A further object of the invention is to provide a personal restraint system capable of maintaining the restrained person in a slightly off-balance position while standing, making it difficult for that individual to escape by foot or to damage property or attack others.

To achieve the foregoing and other objects and in accordance with the purpose of the present invention, as embodied and broadly described herein, the present invention may comprise a personal restraint system for restraining movement of a restrained individual's hands relative to their feet. The restraint system includes lockable pairs of ankle and wrist cuffs and an adjustable strap or web disposed therebetween and interconnected therewith. The wrist cuffs are placed on the restrained individual with his or her hands positioned, preferably behind their back, and more preferably in the downward position near the individual's waist.

The length of the strap or web may be adjusted, preferably by use of a cam buckle between two portions of the belt in order to fit differing sized individuals, to adjust tension, and to allow the restrained individual to assume a sitting position for transport in an automobile, or a standing position for walking.

BRIEF DESCRIPTION OF THE DRAWINGS

The accompanying drawings which are incorporated in and form a part of the specification, illustrate an embodiment of the present invention and, together with the description, serve to explain the principles of the invention.

DETAILED DESCRIPTION OF THE INVENTION

Figure 1:
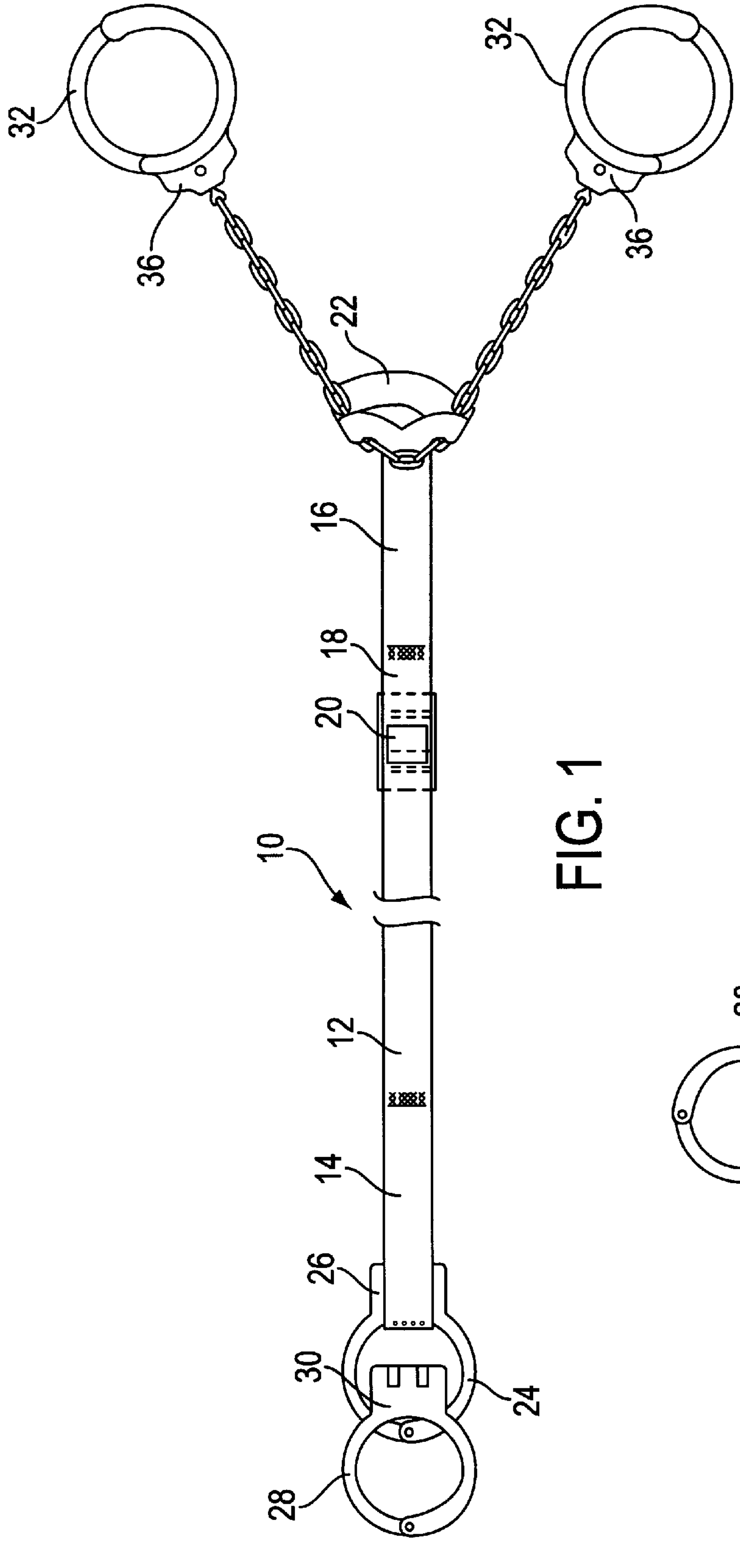
FIG. 1 is a plan view of the personal restraint device of the present invention illustrating pairs of wrist cuffs, ankle cuffs, and a strap therebetween adjustable in length.
Figure 2:
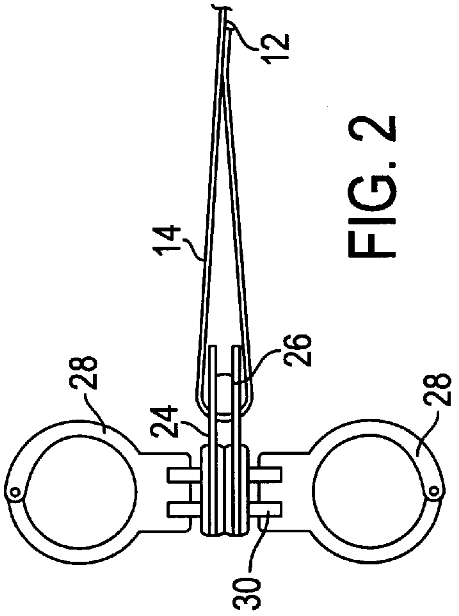
FIG. 2 is an elevation view of the wrist cuffs and their connection.

The present invention overcomes prior art restraint device shortcomings by providing personal restraint system for restraining movement of a restrained individual's hands relative to their feet.

The restraint system of the present invention includes an upper control strap about 50 inches long. The upper control strap has a fixed loop of about 6 inches in length when laid flat. The opposing end serves as a hand grip and is fed through a cam buckle, allowing the strap to move through the buckle when the buckle is open and to be secured at a given point when the buckle is closed. The opposing end also has a safety lock to avoid the strap to completely exit the cam buckle. Also attached to the cam buckle is a fixed length loop of about 6 inches in length made of the same strap material. The upper control strap and lower strap loop are preferably made of 1 inch, tubular nylon woven web. The safety lock is made of plastic and the cam buckle is made of coated aluminum alloy and is properly sized for use with the strap. The restraint system of the present invention includes a pair of standard hinged handcuffs attached to the upper control strap by means of the fixed loop therein. In a second pair of hinged handcuffs, attached to the restrained individual, are locked to the restraint system by the first pair of handcuffs. The restraint system of the present invention also includes standard leg shackles consisting of ankle cuffs interconnected by a chain or the equivalent. The leg shackles are attached to the restraint system by means of the lower loop wrapped about the leg shackle chain.

Referring to FIGS. 1–4, personal restraint system 10 includes upper control strap 12 having fixed loop 14 and lower strap loop 16. Lower strap loop 16, when laid flat forms bottom loop end 18 which is fixedly attached to cam buckle 20 such as by looping through cam buckle 20, and opposing lower strap loop end 22. Upper control strap 12 is fed through cam buckle 20 such that it can alternately be fixedly engaged thereby or allowed to freely slide therethrough by appropriate activation of cam buckle 20 and deactivation of cam buckle 20, respectively. First hinged handcuffs 24 are mounted on fixed loop 14 at hinge 28. Second hinged handcuffs 28 are looped through and bear against first hinged handcuffs 24 at hinge 30. Leg shackles 32 are attached by chain 34 at hinge locks 36, respectively. Chain 34 is looped through lower strap loop 16 at its end 22, chain 34 being held at a point equidistant from its attachments at hinge locks 36 of leg shackles 32 by means of an appropriate knot in lower strap loop 16.

Figure 3:
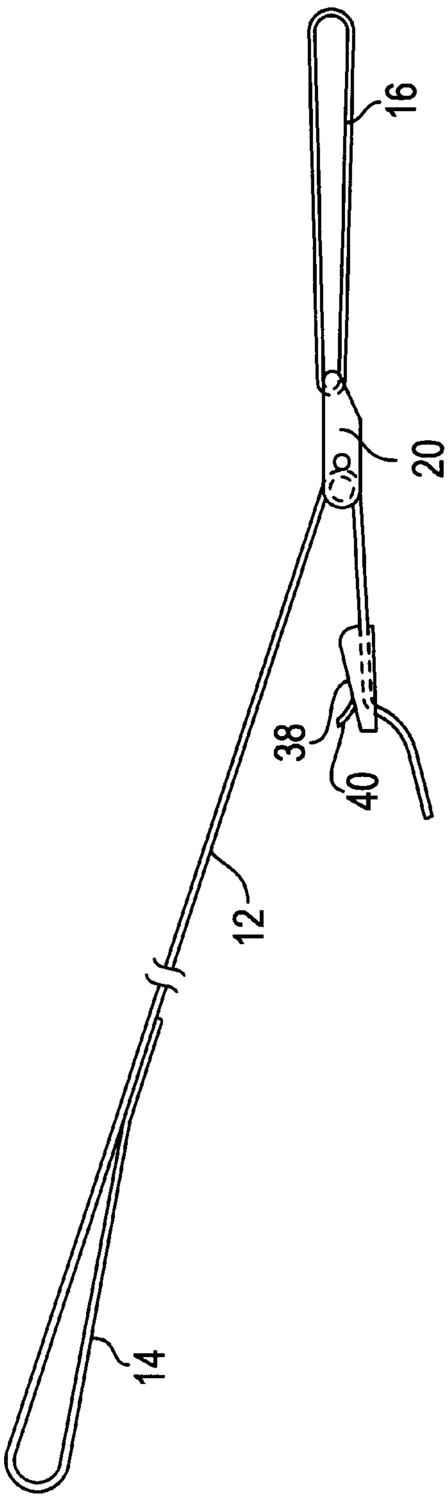
FIG. 3 is a detail view in elevation of the adjustable strap and cam buckle subassembly.
Figure 4:
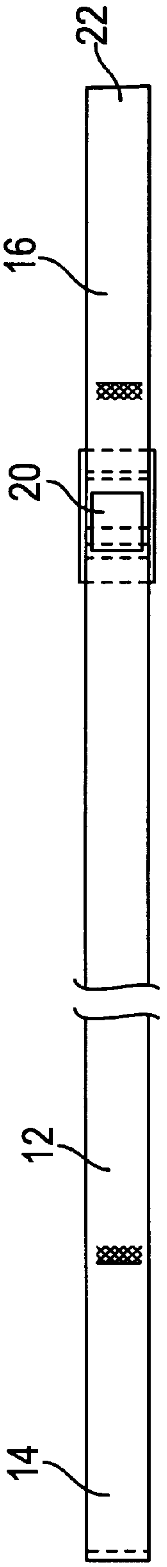
FIG. 4 is a view in plan of the adjustable strap and cam buckle subassembly.

Referring more particularly to FIG. 3, safety lock 38 is mounted on upper control strap 12 near its free end 40. Safety lock 38 can be disengaged, slid along strap 12 to cam buckle 20. and engaged for added security. Safety lock 38, in this position will prohibit strap 12 from sliding through cam buckle 20 if for any reason of cam buckle 20 is disengaged accidentally.

The purpose of the restraint system of the present invention is to assist law enforcement and emergency medical agencies control combative subjects in a safe manner. The inventive restraint system is designed upon application to the wrists and ankles behind a subject to take the subject off their center of gravity and limit the movement of their legs and arms while still allowing the subject to sit upright and walk with assistance. An open clear airway in the subject's throat is thus maintained at all times, avoiding choking. The inventive restraint system can also be adjusted to the size of the subject and loosened of the subject has become compliant. The inventive restraint system can also be used on subjects who have a history of becoming combative in a loosened position. A simple pull on the end of the upper control strap will control the subject. The restraint system incorporates the use of standard leg shackles.

In operation, the inventive restraint system 10 is set on the leg shackles 32 by looping around the connecting chain 34 through the bottom loop 16, centering the loop 16 on chain 34 of the leg shackles by an appropriate knot in loop 16, and then pulling the lower strap loop 16 tight. The leg shackles are then ready to attach to the ankles of the subject. Handcuffs 28 are placed on the wrists of the subject with one hand on the top of the other. The combat stack position is preferred, but may be used with the standard handcuff position. Handcuffs 24 are doubled on its hinge in the open position through fixed loop 14, and then handcuffs 24 are locked around handcuffs 28 near hinge 30, such that handcuffs 24 are secured to fixed strap loop 14 by means of handcuffs 24 locking around hinge 30 of handcuffs 28. Since handcuffs 28 are mounted on the subject, they cannot slide off handcuffs 28. Tension is applied to the restraint system 10 by pulling the end 40 of the top strap 12 relative to the cam buckle 20. Once the desired tension is made, the safety lock 38 will be slid down therealong strap 12 to the cam buckle 20, and locked. To loosen, the safety lock 20 is slid up the strap 12 and then the strap is then loosened through the disengaged cam buckle 20.

The cam buckle 20 is commercially available and well known type. The strap material used in the construction of upper control strap 12 and lower strap loop 16 is preferably one-inch woven tubular nylon web material which is commercially available and widely used for various strapping applications. The size of the cam buckle 20 is selected to operate effectively with the particular width of strap material employed. The cam buckle operates in a well known manner, clamping firmly the top strap 12 when closed or activated and allowing the top strap 12 to slide through when the lever portion of the buckle is urged open, such as when the free end of the top strap 12 is pulled at an angle to the orientation of the tensioned portion of the top strap which is secured to the wrists of the restrained individual. the cam buckle may be spring loaded if desired to maintain the buckle in a closed position except when urged open as described above.

The particular sizes and equipment discussed above are cited merely to illustrate a particular embodiment of the invention. It is contemplated that the use of the invention may involve components having different sizes and shapes as long as the principle, i.e., the provision of a personal restraint system having leg shackles and handcuffs with a means adjustable in length connected therebetween to limit relative movement of a restrained subject's arms and legs, as described above is followed.

We claim:

1. A restraining device for use in combination with a prisoner hand binding comprising:

A. an elongate upper control strap having a fixed length loop at one end for engagement with said hand binding and the opposite end providing a hand grip;

B. a releasable buckle means receiving said control strap opposite end therethrough to define a selected length of control strap between said control strap fixed loop and said buckle means; and C. a lower strap loop connecting said buckle means and leg shackles.

D. said restraining device further comprising lock means located on and slidably engaged with said opposite end of said elongate upper control strap for alternate engagement and disengagement with said releasable buckle means, thereby alternately locking said buckle means against said adjustment of strap length between said hand binding and said leg shackles, and allowing adjustment of said buckle means and thus said strap length;

whereby hand grip control of said upper control strap enables immediate adjustment of the strap length between said hand binding and said leg shackles.

2. A restraining device as in claim 1 wherein said upper control strap and said lower strap loop are constructed of nylon webbing.

3. A restraining device as in claim 1 wherein said releasable buckle means comprises a cam buckle having a spring urged cam holding said control strap in a selected position.

4. The restraining device of claim 1 wherein said leg shackles comprise a pair of ankle cuffs worn by said prisoner and an elongated chain fastened at either end thereof to each said ankle cuffs, said lower strap loop being attached to said chain by a knot.

5. The restraining device of claim 1 wherein said hand binding comprises a first hinged handcuff pair for placement on the wrists of said prisoner, and handcuff attachment means for attachment of said fixed length loop of said upper control strap with said first hinged handcuff pair.

6. The restraining device of claim 5 wherein said handcuff attachment means comprises a second hinged handcuff pair disposed through said fixed loop of said upper control strap and around said first hinged handcuff pair between the wrists of said prisoner.

7. An article of manufacture for use on a person in handcuffs as a further physical restraint, comprising;

A. an elongate upper control strap having a hand grip on one end, and a fixed length loop at the opposite end for engaging said handcuffs;

B. a cam buckle receiving said control strap therethrough for selective locking engagement by said cam buckle;

C. leg shackles having a chain attached therebetween;

D. a lower strap loop connecting to said cam buckle engaging said chain between said leg shackles; and E. a strap lock located on said hand grip end of said elongate upper control strap.

* * * * *